United States Patent
Armstrong (10) Patent No.: US 9,209,589 B2
(45) Date of Patent: Dec. 8, 2015

(54) REDUCING THE SPECTRAL BANDWIDTH OF LASERS

(71) Applicant: KLA-Tencor Corporation, Milpitas, CA (US)

(72) Inventor: J. Joseph Armstrong, Fremont, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 14/607,515

(22) Filed: Jan. 28, 2015

(65) Prior Publication Data

US 2015/0139255 A1  May 21, 2015

Related U.S. Application Data

(62) Division of application No. 13/939,000, filed on Jul. 10, 2013, now Pat. No. 8,964,798.

(60) Provisional application No. 61/670,926, filed on Jul. 12, 2012.

(51) Int. Cl.

| | |
|---|---|
| *H01S 3/30* | (2006.01) |
| *H01S 3/067* | (2006.01) |
| *H01S 3/10* | (2006.01) |
| *H01S 3/02* | (2006.01) |
| *H01S 3/00* | (2006.01) |
| *G01N 21/00* | (2006.01) |
| *G01N 21/95* | (2006.01) |
| *G01N 21/956* | (2006.01) |

(52) U.S. Cl.
CPC ............ *H01S 3/06754* (2013.01); *G01N 21/00* (2013.01); *H01S 3/0057* (2013.01); *H01S 3/02* (2013.01); *H01S 3/06758* (2013.01); *H01S 3/10* (2013.01); *H01S 3/30* (2013.01); *G01N 21/9501* (2013.01); *G01N 21/956* (2013.01); *H01S 3/0092* (2013.01); *H01S 3/302* (2013.01); *H01S 2301/08* (2013.01)

(58) Field of Classification Search
USPC .......................... 372/4, 6, 21–22, 29.021, 69
See application file for complete search history.

(56) References Cited

U.S. PATENT DOCUMENTS

| | | |
|---|---|---|
| 2007/0103765 A1 | 5/2007 | Fermann et al. |
| 2007/0273960 A1 | 11/2007 | Fermann et al. |
| 2008/0013163 A1 | 1/2008 | Leonardo et al. |
| 2008/0130099 A1 | 6/2008 | Harter |
| 2009/0122819 A1 | 5/2009 | Dantus et al. |
| 2009/0185588 A1 | 7/2009 | Munroe |
| 2012/0002688 A1 | 1/2012 | Munroe |
| 2012/0294323 A1* | 11/2012 | Lin ................................ 372/25 |

FOREIGN PATENT DOCUMENTS

JP  2008135673 A  6/2008

* cited by examiner

*Primary Examiner* — Dung Nguyen
(74) *Attorney, Agent, or Firm* — Beaver, Hoffman & Harms, LLP (57) ABSTRACT

A laser system for semiconductor inspection includes a fiber-based fundamental light source for generating fundamental light that is then converted/mixed by a frequency conversion module to generate UV-DUV laser light. The fundamental light source includes a nonlinear chirp element (e.g., a Bragg grating or an electro-optic modulator) that adds a nonlinear chirp to the seed light laser system prior to amplification by the fiber amplifier(s) (e.g., doped fiber or Raman amplifiers). The nonlinear chirp includes an $x^2$ or higher nonlinearity and is configured to compensates for the Self Phase Modulation (SPM) characteristics of the fiber-based amplifiers such that fundamental light is generated that has a spectral E95 bandwidth within five times that of the seed light. When multiple series-connected amplifiers are used, either a single nonlinear chirp element is provided before the amplifier string, or a chirp elements are included before each amplifier.

18 Claims, 9 Drawing Sheets

REDUCING THE SPECTRAL BANDWIDTH OF LASERS

RELATED APPLICATIONS

This application is a divisional of U.S. patent application Ser. No. 13/939,000 entitled "Reducing The Spectral Bandwidth Of Lasers" filed Jul. 10, 2013, which claims priority to U.S. Provisional Patent Application 61/670,926, entitled "Reducing The Spectral Bandwidth Of Lasers" filed Jul. 12, 2012.

BACKGROUND OF THE INVENTION

1. Field of the Invention

The present invention generally relates to illuminators used in conjunction with inspection systems, such as semiconductor wafer inspection systems and photomask inspection systems, and more particularly to a fiber amplifier based light source for use with such inspection systems.

2. Description of the Related Art

Figure 1A:
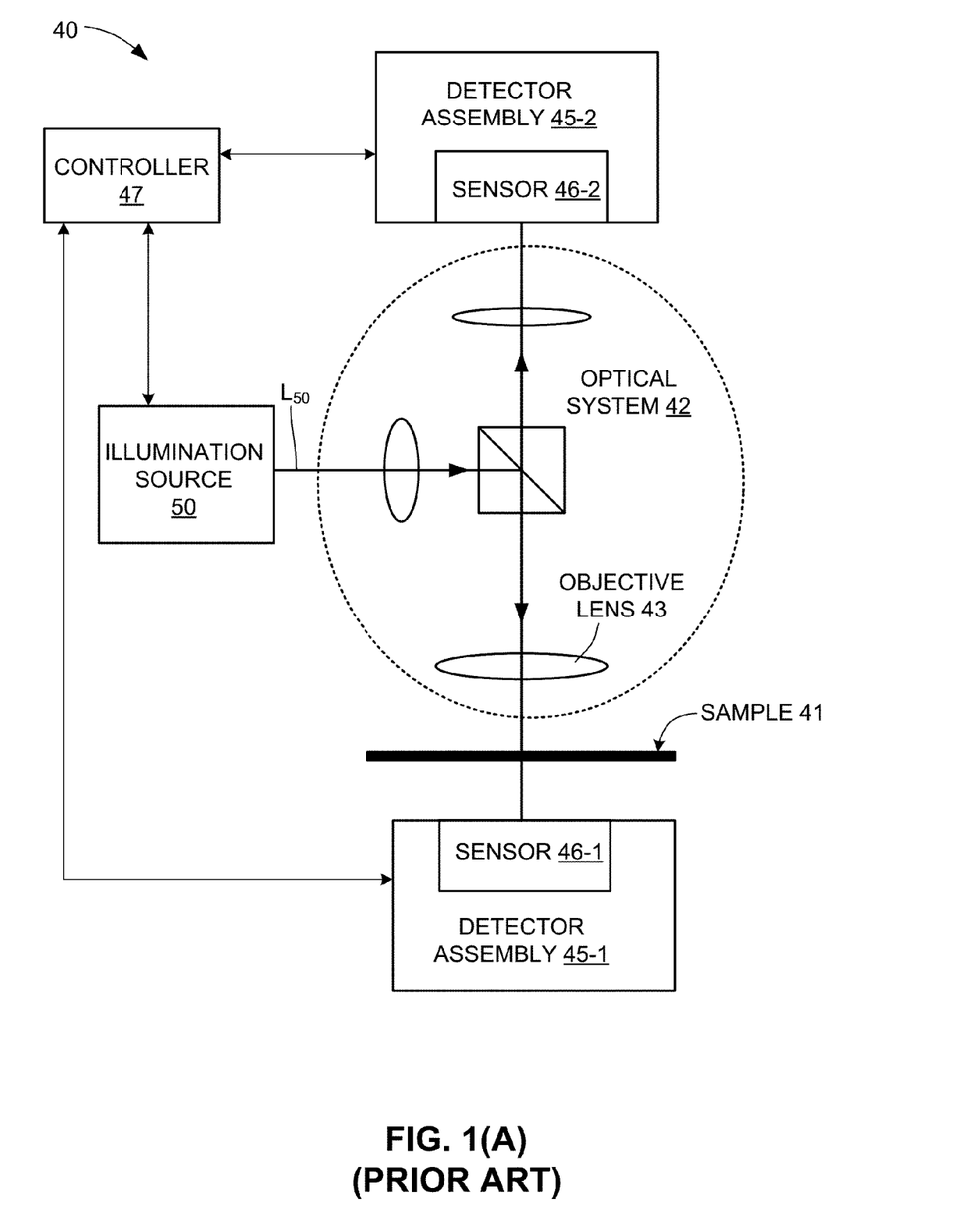
FIG. 1(A) is a simplified block diagram illustrating a laser inspection system.

FIG. 1(A) is a diagram depicting a simplified UV-DUV laser inspection system 40 utilized in the semiconductor industry for inspecting a target sample (e.g., a wafer or photomask/reticle) 41. Inspection system 40 includes an illumination source 50 that generates laser light $L_{50}$ typically in the UV-DUV range (e.g., less than 350 nm), an optical system 42 including one or more objective lenses 43 that focus the laser light onto sample 41, a pass-through detector assembly 45-1 including a sensor array 46-1 positioned to receive any laser light that passes through sample 41 (e.g., for purposes of inspecting a photomask/reticle), and a reflected light detector assembly 45-2 including a sensor array 45-2 positioned to detect any laser light that is reflected from sample 41 (e.g., for purposes of inspecting wafer surface features). A controller (computing system) 47 controls the operation of the various subsystems according to a software operating program, and processes image data received from detector assemblies 45-1 and 45-2 using techniques known in the art.

It is understood that, in general, lower frequency laser light produces higher resolution images, which in a laser inspection system provides better information regarding features and defects on the imaged samples. To meet the increasing demand for laser inspection systems having ever higher resolution, the current trend in the semiconductor industry is toward the development of low frequency UV-DUV laser inspection systems (i.e., systems utilizing laser light below 250 nm). For example, the assignee of the present application is currently working to develop low frequency UV-DUV laser inspections systems operating with 213 nm, 206 nm or 193 nm laser light.

A significant obstacle to the development of low frequency UV-DUV laser inspection systems is to provide an optical system that can effectively image the UV laser light. The only two practical materials available for generating the various lenses and elements for the optical system of a UV-DUV laser inspection system (e.g., optical system 42 in FIG. 1(A)) are fused silica and calcium fluoride, with fused silica being preferred because calcium fluoride is much more expensive to obtain, polish and mount. Optical systems manufactured from all fused silica for use in systems using UV-DUV laser light can only handle a limited bandwidth before the performance degrades beyond acceptable limits. Specifically, the larger the numerical aperture (NA) and field size, and the shorter the wavelength, the smaller the acceptable bandwidth can be. For example, an all refractive objective at 266 nm with 0.8NA and 1.0 mm field of view may only achieve a bandwidth of 5 pm. One approach to deal with a larger bandwidth this is to reduce the glass path by using aspheric surfaces because a single aspheric surface may eliminate several equivalent spherical lenses. However the increased cost and complexity associated with the use of aspheric surface may not be desirable, and this approach only helps a small amount in most laser systems.

To minimize the cost and complexity required to generate optical system 42 for low frequency UV-DUV laser inspection system 100, illumination source 50 must be able to generate laser light $L_{50}$ in which substantially all of the light energy is within a narrow bandwidth. It is typical to specify the bandwidth of a laser light source using a full width half maximum (FWHM) value, which specifies the light's bandwidth range at one-half of the light's peak power. However, in UV-DUV laser inspection systems, the bandwidth range at which 95% of the energy is contained (i.e., the light's "E95" bandwidth value) is the more important value. A typical illumination source 41 generates laser light $L_{50}$ having a relatively narrow FWHM bandwidth value, but having an E95 value that is ten or more times broader then it's FWHM. It is therefore important in laser imaging system 40 to utilize an illumination source 50 that generates narrow band UV laser light $L_{50}$ that is both low frequency UV (e.g., laser light having a nominal frequency value below 250 nm) and has a narrow E95 bandwidth (i.e., within ±1%, and preferably within ±0.1%, of the nominal or "central" UV frequency).

Narrow band UV light is typically created by generating fundamental light having a longer wavelength (typically longer than 1 micron), and then converting the fundamental light using crystals that perform nonlinear frequency conversion and frequency mixing to generate UV light having a desired (shorter) wavelength. Because of limitations on the frequency conversion/mixing process, the fundamental light must have a specific higher frequency in order to generate UV light at a specified lower frequency. It is also possible to perform the frequency conversion/mixing process using other nonlinear processes (e.g., Raman, parametric generation, and four wave mixing (FWM)), but these techniques can also lead to increased bandwidths and not be suitable for narrow bandwidth optics. Many stages of frequency conversion/mixing are sometimes needed to generate shorter wavelength light having a specified frequency, and power is lost from the light during each frequency conversation stage. Therefore, in order to generate UV laser light at an acceptable power, it is necessary to generate the fundamental light at significantly higher peak power than is needed at the optical system.

There are two types of fundamental light sources used in the generation of narrow band UV light: solid state lasers and fiber lasers. Solid-state lasers can produce laser light having very narrow bandwidths and high peak power, which allows for the use of less complex (and therefore lower cost) optical systems, but the wavelength choices for solid state lasers are very limited and not suitable for laser inspection systems, and it can be very challenging to obtain reliable high power light from a solid state laser. Fiber lasers include an active gain medium formed by an optical fiber doped with rare-earth elements such as Erbium, Ytterbium, Neodymium, Dysprosium, Holmium, Praseodymium, and Thulium. Fiber lasers are an attractive choice for generating fundamental light in laser inspection systems because they generate laser light having high peak power, and the frequency of the laser light can be "tuned" to a specified frequency by altering the amounts of doping materials in the fiber(s). However, as described below, the primary drawback of using fiber lasers to generate high peak power pulsed fundamental light is Self Phase Modulation (SPM). In general, SPM is a nonlinear optical effect of light-matter interaction, where ultrashort light pulses travelling in the fiber medium induce a varying refractive index of the medium due to the optical Kerr effect. The variation in refractive index produces a phase shift in the light pulse, leading to a change of the pulse's frequency spectrum. The nonlinear SPM effect can dramatically increase the spectral bandwidth of a fiber laser well beyond the optical requirements of a laser inspection system.

Figure 1B:
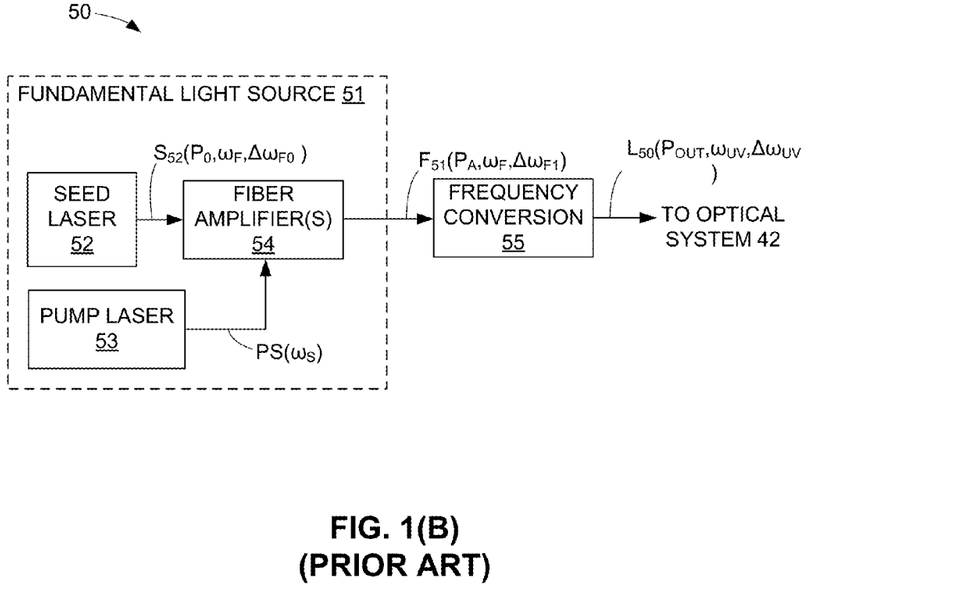
FIG. 1(B) is a simplified block diagram illustrating a conventional pulsed fiber laser.

FIG. 1(B) is a diagram showing a conventional fiber-based illumination source 50, which is utilized to generate UV laser light $L_{50}$ in inspection system 40 (shown in FIG. 1(A)). Fiber-based illumination source 50 generally includes a fundamental light source 51 for generating fundamental light $F_{51}$ at a specified fundamental frequency $\omega_F$, and a frequency conversion module 55 that performs the frequency conversion/mixing process mentioned above in order to generate UV laser light $L_{50}$ at a specified UV frequency $\omega_{UV}$ that is passed to optical system 42 (see FIG. 1(A)). Fundamental light source 51 includes a seed laser 52 that generates seed light $S_{52}$ having the desired fundamental light frequency $\omega_F$ at an initial power $P_0$, a pump laser 53 that generates pump seed light PS at a suitable seed frequency $\omega_S$, and one or more fiber amplifiers 54 that utilize the pump seed light PS to amplify seed light $S_{52}$ in a manner understood in the art, whereby fundamental light $F_{51}$ is produced having the desired fundamental frequency $\omega_F$ and an amplified power $P_A$ that is substantially higher than initial power $P_0$. Fundamental light $F_{51}$ is then converted/mixed by frequency conversion module 55 to generate UV laser light $L_{50}$ having the desired UV frequency $\omega_{UV}$, but at an output power $P_{OUT}$ that is substantially lower than the amplified power $P_A$ of fundamental light $F_{51}$ (i.e., due to energy losses during the conversion/mixing process).

As mentioned above, fundamental light $F_{51}$ has a bandwidth $\Delta\omega_F$ that is determined in part by the SPM characteristics of fiber amplifier(s) 54, as is well known in the art, and is described in many text books including, "Nonlinear Fiber Optics", by Govind P. Agrawal (Academic Press; 5 edition (Oct. 24, 2012). SPM gives rise to a phase shift during the amplification process that is intensity dependent given by:

$$\phi_{NL}(L, T) = |U(O, T)|^2 \left(\frac{L_{eff}}{L_{NL}}\right)$$

where $$L_{eff} = \frac{1 - \exp(-\alpha L)}{\alpha}$$

and $$L_{NL} = \frac{1}{\gamma P_0}$$

In the above equations, $\phi_{NL}$ is the intensity dependent phase shift, L is the fiber length, T is time, U is the energy distribution, $\alpha$ is the fiber loss, $L_{eff}$ is the effective length of the fiber considering fiber loss, $L_{NL}$ is the fiber length at which significant SPM occurs, $P_0$ is the peak power of the pulse, and $\gamma$ is the nonlinear coefficient. Because one of the seed light $S_{52}$ or the pump seed light PS are pulsed, the intensity $\phi_{NL}$ changes in time, and this produces a phase that changes in time as well. When the phase of light changes in time, this creates changes in the wavelength spectrum. The spectral shift $\delta\omega(T)$ relative to the central frequency value is given by $$\delta\omega(T) = -\frac{\partial \phi_{NL}}{\partial T} = -\left(\frac{L_{eff}}{L_{NL}}\right)\frac{\partial}{\partial T}|U(0, T)|^2$$

Spectral shift $\delta\omega(T)$ is also known as a chirp, or change in the instantaneous frequency across the pulse.

Figure 2A:
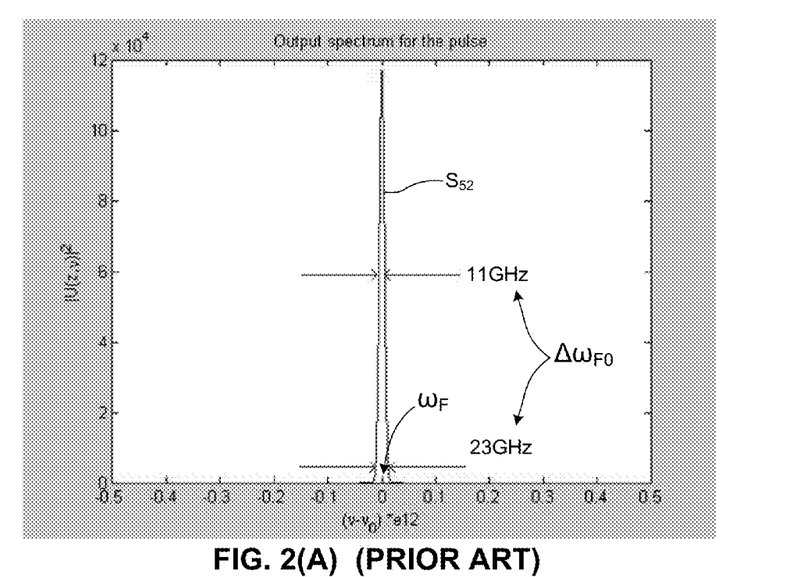
FIG. 2(A) is an output spectrum diagram showing a seed pulse generated by the seed laser in the pulsed fiber laser of FIG. 1(B)
Figure 2B:
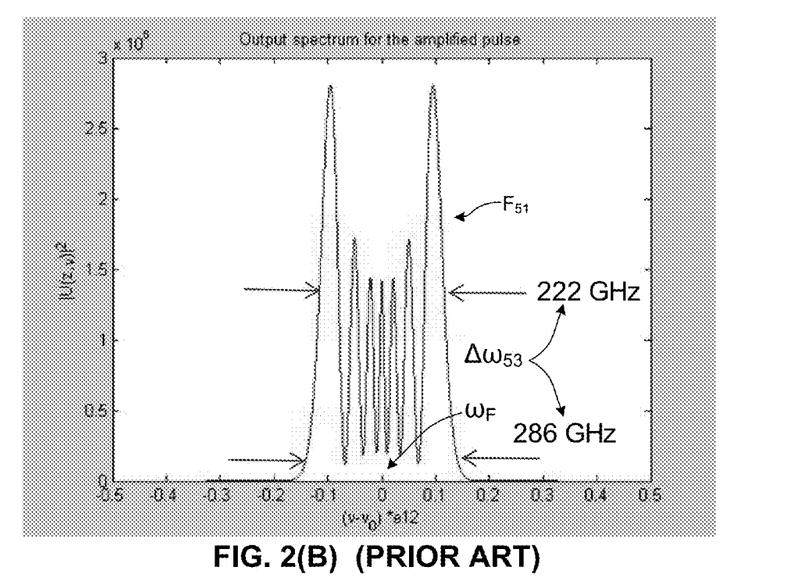
FIG. 2(B) is an output spectrum diagram showing amplified light and illustrating the effect of Self Phase Modulation on the spectral bandwidth of a fiber laser.

FIGS. 2(A) and 2(B) are optical spectrum diagrams showing examples of a seed pulse $S_{52}$ and a fundamental light pulse $F_{51}$ generated by conventional fundamental light source 51 (shown in FIG. 1(B)), and illustrate the output bandwidth produced by the intensity dependent phase shift generated in conventional fiber-based illumination source 50 (FIG. 1(B)). FIG. 2(A) shows that fundamental seed light $S_{52}$ is an initial transform limited Gaussian pulse has a peak power of approximately $6 \times 10^6$ centered around a fundamental frequency $\omega_F$ (e.g., 1030 nm) and having an FWHM value of 11 GHz and an E95 energy bandwidth of 23 GHz. FIG. 2(B) shows fundamental light pulse $F_{52}$, which is produced in amplifier 54 (FIG. 1(B)) using seed light pulse $S_{52}$ and pump seed light PS. FIG. 2(B) shows that fundamental light pulse $F_{52}$ remains generally centered around fundamental frequency $\omega_F$ while being amplified to a peak power $P_A$ of 10 kW. However, due to the SPM characteristics of fiber amplifier(s) 54, the FWHM value of fundamental light pulse $F_{52}$ increases to 222 GHz, and exhibits an E95 energy bandwidth of 286 GHz. This roughly tenfold increase in E95 energy exhibited by fiber-based fundamental light sources is impractical for generating the type of narrow band UV light needed in modern laser inspection systems.

What is needed is a fundamental light source that combines the high peak power and frequency-tuning capability of fiber-based lasers with the simplified (low cost) optical systems typically associated with solid-state lasers.

SUMMARY OF THE INVENTION

The present invention is directed to a fiber-based fundamental light source for generating fundamental light F in a laser system in which seed light and/or partially amplified light is modified to include a nonlinear chirp that compensates for the Self Phase Modulation (SPM) characteristics of the fiber-based amplifiers, whereby fundamental light is generated having both high peak power and a narrow bandwidth. According to a practical embodiment, the laser system also includes a frequency conversion module that converts the fundamental light generated by the fiber-based fundamental light source from a relatively high fundamental frequency (e.g., 1030 nm) to generate laser output light L at a desired low UV-DUV frequency (e.g., 213 nm, 206 nm or 193 nm) that is directed to an associated optical system. By using a compensating nonlinear chirp to compensate for SPM prior to completion of the fiber-based amplification process, the present invention facilitates the cost-effective manufacture of high resolution laser inspection systems by combining the high peak power and frequency-tuning capability of fiber-based lasers with the simplified optical systems typically associated with solid-state lasers.

According to an aspect of the present invention, one or more nonlinear chirp elements (e.g., Bragg gratings, fiber Bragg gratings or electro-optic modulators) are utilized to generate the compensating nonlinear chirp, and the nonlinear chirp has a nonlinearity on the order of $x^2$ or higher. In a specific embodiment, the nonlinear chirp U(0,T) has a time-based frequency characterized by the equation $$U(0, T) = \exp\left[-\frac{(1 + i(C + DT + ET^2 + FT^3 + GT^4 + \ldots))}{2} \frac{T^2}{T_0^2}\right]$$

where T is time, i indicates the imaginary part of the amplitude that contains the phase term, and wherein at least one of one of E, F and G is non-zero. The present inventor has determined that a nonlinear chirp having a nonlinearity of $x^2$ or higher is required to achieve fundamental light having a narrow spectral E95 bandwidth that is in a range defined by five times the (initial) spectral E95 bandwidth of the seed light generated by the seed laser (e.g., in the range of 1 and 100 GHz). By way of comparison, a linear chirp generated in a manner similar to that used in the present invention (e.g., using a Bragg grating configured to generate a linear chirp) is capable of generating a FWHM value that is close to that of the seed light, but its E95 bandwidth is over ten times higher. Accordingly, the SPM characteristics generated by a fiber-based amplifier (e.g., either a doped fiber amplifier or a fiber Raman amplifier) require an $x^2$ or higher nonlinearity (e.g., that at least one of E, F and G in the above equation must be non-zero) to adequately compensate for SPM characteristics to the degree required by high resolution laser inspection systems. According to an embodiment, a single nonlinear chirp element is positioned in the laser optical path between the seed laser and a series of fiber amplifiers, wherein the nonlinear chirp element is configured to generate a single nonlinear chirp that compensates for the cumulative SPM generated by all of the series-connected fiber amplifiers. A benefit of this single element approach is that the seed/amplified light encounters a minimum number of nonlinear chirp element, thereby minimizing power loss. According to an alternative embodiment, a nonlinear chirp element is positioned in the laser light optical path in front of each of the series-connected fiber amplifier, wherein each nonlinear chirp element is configured to generate a component nonlinear chirp that compensates for individual SPM characteristics associated with the subsequent fiber amplifier. A benefit of this multiple-element approach is that it simplifies the compensating nonlinear chirp calculation by addressing the SPM characteristics of each fiber amplifier (i.e., instead of having to calculate a compensating nonlinear chirp for the cumulative SPM of multiple series-connected amplifiers).

According to another embodiment of the present invention, a Raman amplifier receives both continuous wave (CW) seed light and pulsed pump seed light, and the nonlinear chirp NLC is added to the CW seed light by a phase modulator. Subsequent "downstream" series-connected Raman amplifiers receive pulsed pump seed light, but not CW seed light. A benefit of utilizing this Raman amplifier approach is the Raman spectral shift allows the laser to operate at high power levels at wavelengths outside the range that is possible with standard fiber lasers.

These and other advantages of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which.

DETAILED DESCRIPTION

The present invention relates to an improvement in laser technology. The following description is presented to enable one of ordinary skill in the art to make and use the invention as provided in the context of a particular application and its requirements. As used herein, directional terms such as "higher", "lower", "front" and "downstream" are intended to provide relative positions for purposes of description, and are not intended to designate an absolute frame of reference. Various modifications to the preferred embodiment will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 3:
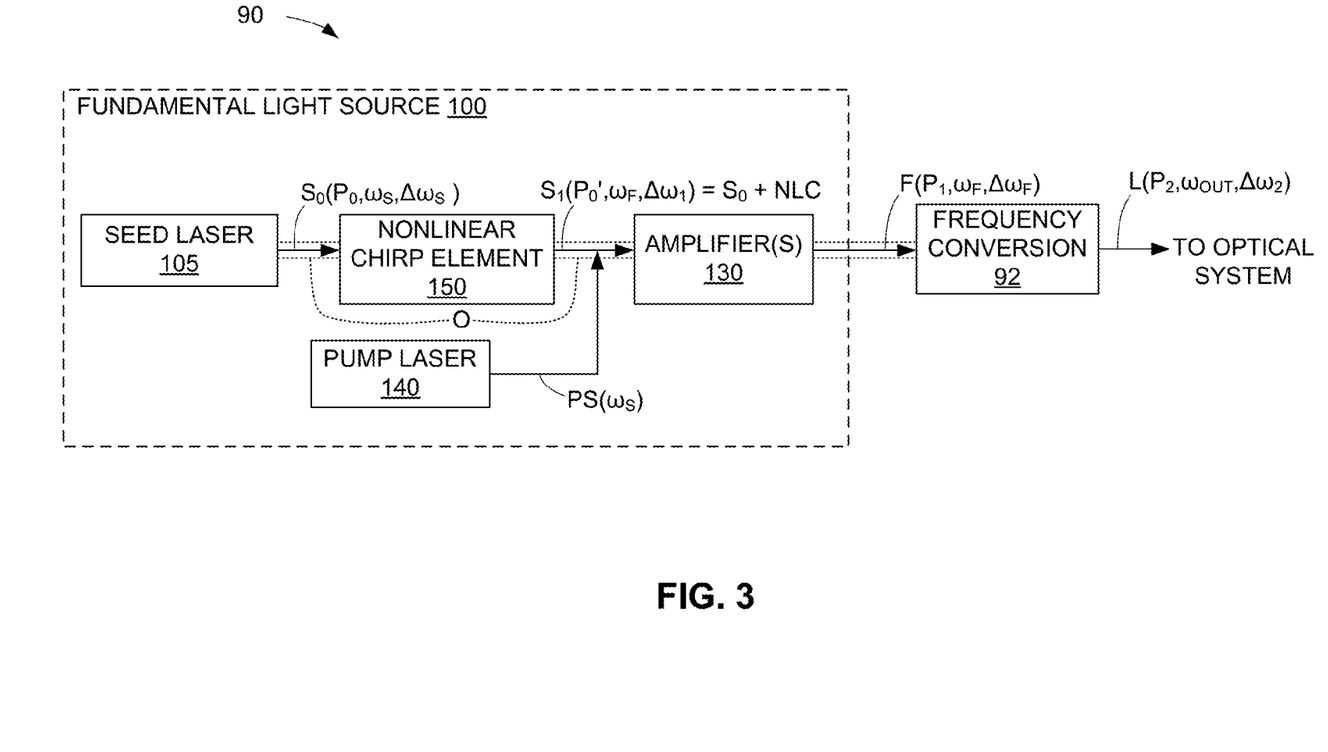
FIG. 3 is a simplified block diagram showing a laser system according to a generalized embodiment of the present invention.

FIG. 3 shows a laser system 90 according to a generalized embodiment of the present invention. Laser system 90 includes a fiber-based fundamental laser system 100 for generating fundamental light F at a nominal fundamental frequency $\omega_F$, and a frequency conversion module 94 including various elements for converting/mixing fundamental light F to generate laser output light L at a desired nominal output frequency $\omega_{OUT}$, which is then passed to an associated optical system (not shown).

According to an embodiment, laser system 90 is utilized as the illumination source in a UV-DUV laser inspection system in the manner described above with reference to FIG. 1(A)). Referring to the right side of FIG. 3, in a specific embodiment, fundamental light F at a nominal fundamental frequency $\omega_F$ that is approximately 1 μm (e.g., 1030 nm), and frequency conversion module 94 is configured to convert fundamental light F to a specified output frequency $\omega_{OUT}$ that is less than 40% of said nominal fundamental frequency $\omega_F$ (e.g., below 400 nm, and more particularly such that laser light L has a nominal frequency of 355 nm, 266 nm, 213 nm, 206 nm or 193 nm). Laser light L also has an output bandwidth $\Delta\omega_{OUT}$ that is proportional to a fundamental spectral bandwidth $\Delta\omega_F$ of fundamental light L. A frequency conversion architecture capable of performing the function of frequency conversion module 94 is disclosed in co-owned and co-pending U.S.

patent application Ser. No. 13/558,318, entitled "Solid-State Laser And Inspection System Using 193 nm Laser", which is incorporated herein by reference in its entirety. Although the present invention is described herein with specific reference to UV-DUV laser inspection system, the present invention is believed to be useful in other laser systems as well.

Referring the left side of FIG. 3, similar to conventional fiber-based lasers, fundamental light source 100 includes a seed laser 105, a fiber-based amplifier 130, and a pump seed laser 140. Seed laser 105 (e.g., a pulsed light oscillator, a solid state laser, a diode laser, a gain-switched laser diode, or a quantum dot laser) generates seed light $S_0$ having an initial (relatively low) peak power $P_0$ and an initial spectral bandwidth $\Delta\omega_S$, and transmits seed light $S_0$ along an optical path O using known techniques. Amplifier 130 is disposed in optical path O and including a fiber-based amplification mechanism (e.g., a doped fiber amplifier or a fiber Raman amplifier) that amplifies the seed light $S_0$ such that fundamental (amplified) light F output from amplifier 130 has a fundamental peak power $P_1$ that is substantially higher (e.g., ten times) than initial peak power $P_0$ of seed light $S_0$. Pump seed laser 140 (e.g., a pulsed light oscillator, a solid state laser, a diode laser, a gain-switched laser diode, or a quantum dot laser) generates and transmits pump seed light PS to amplifier 130 according to known techniques.

According to an aspect of the present invention, fundamental light source 100 includes a nonlinear chirp element 150 disposed in optical path O (e.g., between seed laser 105 and amplifier 130) that combines seed light $S_0$ (or, as explained below, partially amplified seed light) with a nonlinear "pre-chirp" (chirp) NLC that compensates for the inherent SPM characteristics of amplifier 130. In one embodiment, nonlinear chirp element 150 is implemented using a Bragg grating, a fiber Bragg grating or an electro-optic modulator that is configured to generate nonlinear chirp NLC in a manner that "mirrors" the amplifier's SPM characteristics (i.e., such that the frequency bandwidth and frequency amplitudes of the nonlinear pre-chirp NLC are substantially opposite to those of the amplifier's SPM characteristics, whereby the nonlinear chirp NLC compensates for (i.e., effectively cancels or greatly reduces) the amplifier's SPM characteristics such that fundamental spectral bandwidth $\Delta\omega_F$ of fundamental light F is in a range defined by five times said initial spectral E95 bandwidth $\Delta\omega_S$ of seed light $S_0$.

According to another aspect of the present invention, chirp element 150 is constructed to generate nonlinear pre-chirp with a nonlinearity on the order of $x^2$ or higher. Specifically, one or more nonlinear chirp elements 150 constructed to generate a nonlinear pre-chirp $U(0,T)$ having time-based frequency characterized by the equation $$U(0, T) = \exp\left[-\frac{(1 + i(C + DT + ET^2 + FT^3 + GT^4 + \ldots))}{2} \frac{T^2}{T_0^2}\right]$$

where T is time, i indicates the imaginary part of the amplitude that contains the phase term, and wherein at least one of one of E, F and G is non-zero. That is, the equation utilized to generate nonlinear chirp element 150 has at least one time-based component having an order of $T^2$ or higher. Accordingly, nonlinear chirp element 150 is constructed by first measuring and quantifying the SPM characteristics of amplifier 130 using known techniques, then values for C, D, E, F and G are calculated that compensate for (mirror) the measured/quantified characteristics, and then a nonlinear chirp element 150 is constructed to include the requisite compensating non-linear pre-chirp (e.g., a Bragg grating is constructed having a periodic refractive index variation that implements the nonlinearity defined by the calculated values).

Figure 4:
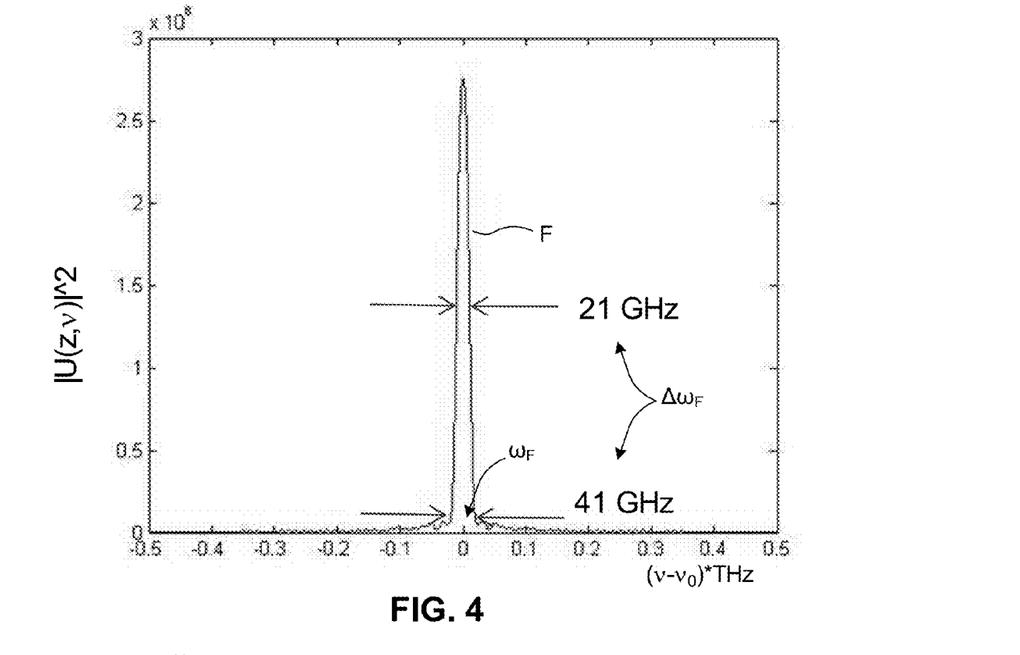
FIG. 4 is an output spectrum diagram showing amplified fundamental light generated by the laser system of FIG. 3.

FIG. 4 shows an exemplary output spectrum diagram for fundamental light F generated from seed pulse using a non-linear pre-chirp according to the present invention. For comparison purposes, the seed pulse utilized in this example is the same as that shown in FIG. 2(A) and described above. Note that fundamental light F is a 10 kW peak power laser pulse having a fundamental spectral bandwidth $\Delta\omega_F$ around a nominal fundamental frequency $\omega_F$ (e.g., 1030 nm), where fundamental spectral bandwidth $\Delta\omega_F$ is characterized by having a FWHM value of 21 GHz (compared to the 11 GHz FWHM value of the seed pulse; see FIG. 2(A)) and a spectral E95 bandwidth of 41 GHz (compared to 23 GHz E95 value of the seed pulse shown in FIG. 2(A)). The substantial improvement provided by adding a nonlinear chirp is clearly indicated by comparing FIG. 4 with FIG. 2(A)—the nonlinear chirp produced a ten-times reduction in FWHM (i.e., from 222 GHz to 21 GHz) and an approximately seven-times improvement in spectral E95 bandwidth (i.e., from 286 GHz to 41 GHz).

Figure 5:
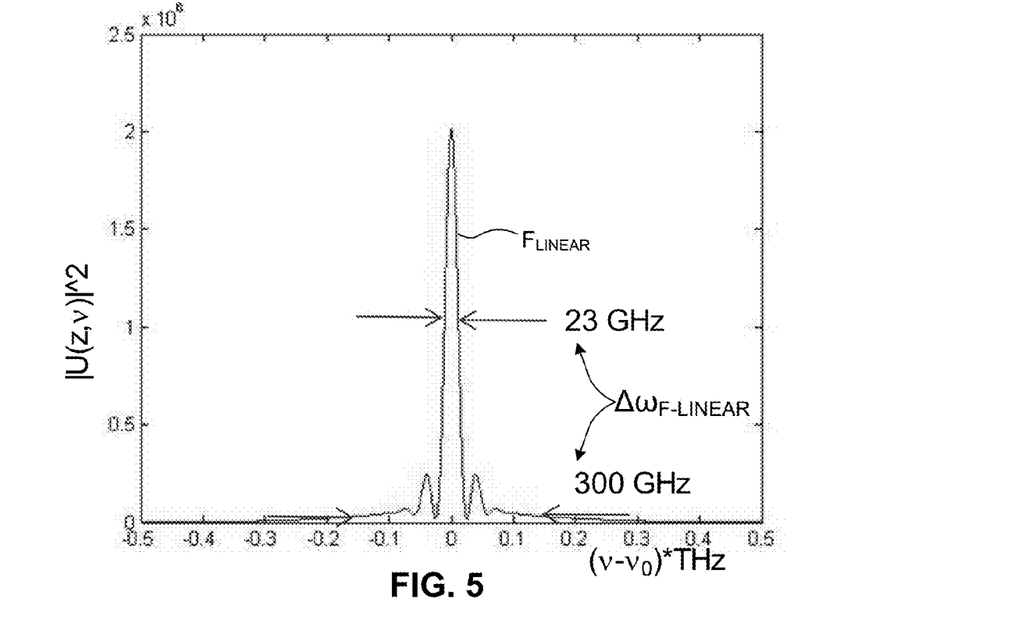
FIG. 5 is an output spectrum diagram showing amplified fundamental light generated using a linear chirp.

For comparison purposes, FIG. 5 shows an output spectrum diagram for fundamental light $F_{LINEAR}$ generated using a linear pre-chirp and having a 10 KW peak power pulse. That is, instead of using a pre-chirp having a nonlinearity of x2 or higher, FIG. 5 illustrates the effect of modifying the seed pulse of FIG. 2(A) using a pre-chirp constructed using the following linear equation (function):

$$U(0, T) = \exp\left[-\frac{(1 + iC)}{2} \frac{T^2}{T_0^2}\right]$$

Similar to the nonlinear example, a linear pre-chirp element is matched using the above equation to the fiber characteristics and the amount of SPM generated by the amplifier so that the inherent SPM chirp is compensated as much as possible. As indicated in FIG. 5, fundamental light $F_{LINEAR}$ exhibits a central spike with a relatively narrow FWHM value similar to that generated by the nonlinear chirp (i.e., 23 GHz). However, as can be seen in the lower portion of FIG. 5, the spectral width of the laser pulse at the E95 energy point is extremely broad (i.e., 300 GHz or more). This large E95 value is present because there is still significant inherent chirp remaining on the pulse that is not linear. As such, it is not believed possible to utilize a linear pre-chirp that sufficiently compensates for the nonlinear SPM characteristics of a fiber-based amplifier to produce the high peak power, narrow bandwidth laser light required for high resolution UV-DUV laser inspection systems.

Referring again to FIG. 3, fundamental laser system 100 is illustrated with a single nonlinear chirp element 150 disposed in optical path O between seed laser 105 and a single amplifier 130. With this arrangement, modified seed light $S_1$ exiting nonlinear chirp element 150 has the same nominal wavelength $\omega_S$, similar peak power $P_0'$ (i.e., peak power $P_0'$ substantially equal to but slightly lower than initial peak power $P_0$ of seed light $S_0$), and a modified spectral bandwidth $\Delta\omega_1$ that is different from said initial narrow spectral bandwidth $\Delta\omega_S$ in that it includes nonlinear chirp NLC. Fiber amplifier 130 includes a fiber-based amplification mechanism that amplifies modified seed light $S_1$ such that said fundamental light F has the required UV-DUV fundamental spectral bandwidth $\Delta\omega_F$. In some embodiments (e.g., in the case where fiber amplifier 130 is a doped fiber amplifier), the nominal fundamental frequency $\omega_F$ of fundamental light F is substantially identical to the initial (seed) frequency $\omega_S$. In other embodiments (e.g., in the case where fiber amplifier 130 is a Raman amplifier), the nominal fundamental frequency $\omega_F$ of fundamental light F is substantially different from initial (seed) frequency $\omega_S$.

Figure 6:
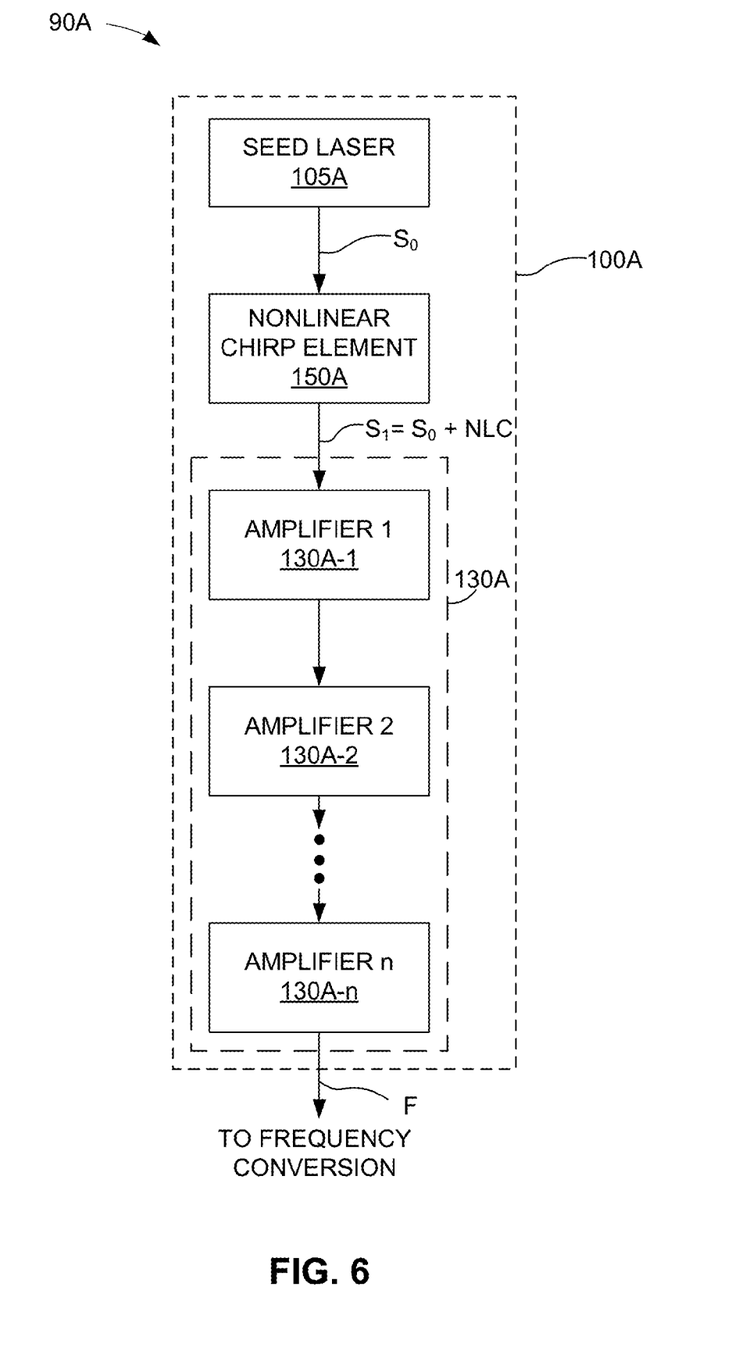
FIG. 6 is a simplified block diagram showing a laser system according to an embodiment of the present invention.

Although the invention is described above with reference to a system including a single fiber-based amplifier 130 for brevity, it is understood that most high peak power fiber-based laser systems utilize two or more series-connected amplifiers to achieve a sufficiently high fundamental light so that the output laser light has an adequate power level. FIG. 6 shows a portion of a laser system 90A according to an embodiment of the present invention in which a fiber-based fundamental laser system 100A includes a single seed laser 105A, an amplifier section 130A including multiple series-connected amplifiers 130A-1, 130A-2 ... 130A-n, and a single nonlinear chirp element 150A that is disposed in the optical path between seed laser 105A and amplifier section 130A. In this case, single nonlinear chirp element 150A is configured to generate a single nonlinear pre-chirp NLC that is added to modified seed light $S_1$ to compensate for the cumulative SPM effect generated by all of series-connected fiber amplifiers 130A-1, 130A-2 ... 130A-n. That is, the cumulative SPM characteristics of series-connected amplifiers 130A-1, 130A-2 ... 130A-n is determined and quantified, and then nonlinear chirp element 150A is constructed to generate a nonlinear pre-chirp that compensates for the cumulative SPM characteristics. A benefit of using single nonlinear chirp element 150A is that this arrangement minimizes power loss to the modified seed light passed to amplifier section 130A.

Figure 7:
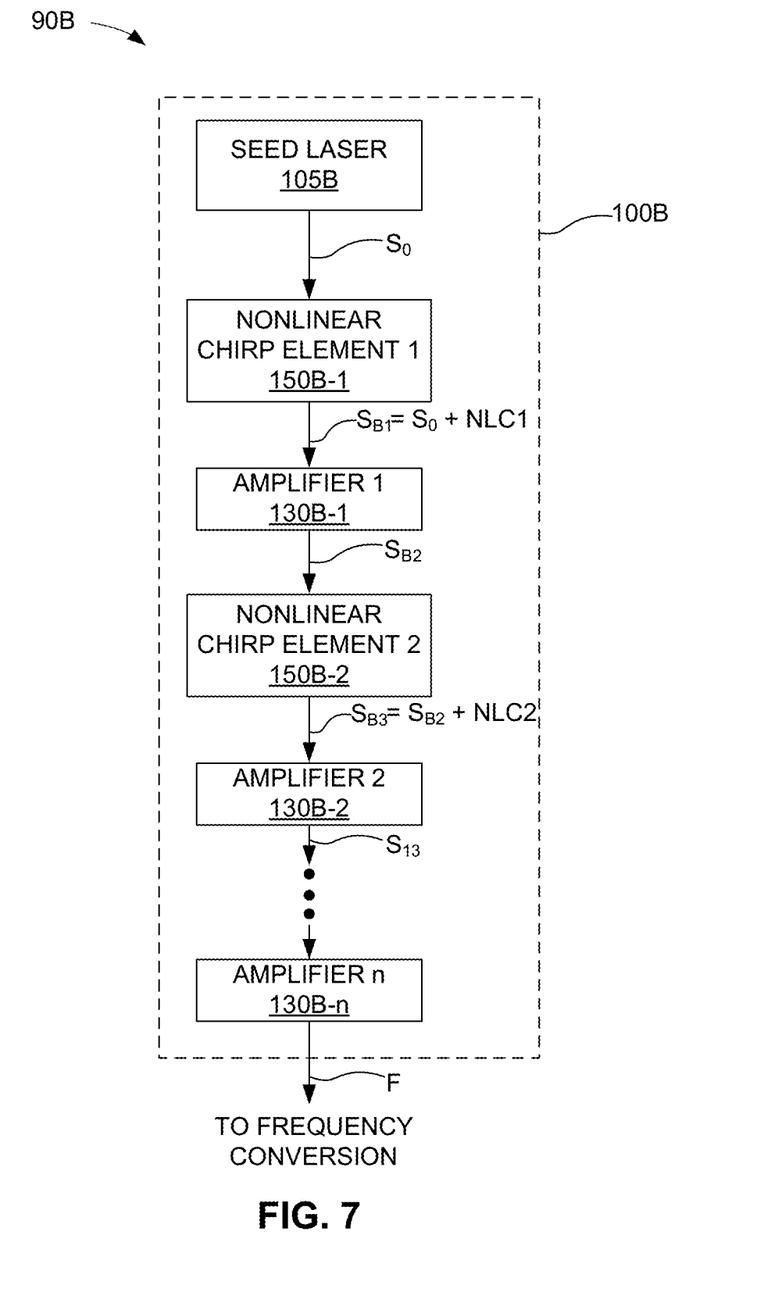
FIG. 7 is a simplified block diagram showing a laser system according to another embodiment of the present invention.

FIG. 7 shows a portion of a laser system 90B according to another embodiment of the present invention in which a fiber-based fundamental laser system 100B includes seed laser 105B, multiple amplifiers 130B-1, 130B-2 ... 130B-n, and multiple nonlinear chirp elements 150B-1, 150B-2 ..., where at least one nonlinear chirp element is disposed in the optical path between two amplifiers (e.g., element 150B-2 is disposed between amplifiers 130B-1 and 130B-2). In this case, each nonlinear chirp element 150B-1, 150B-2 ... is configured to generate a nonlinear pre-chirp that is added either to the seed light or to partially amplified seed light (e.g., nonlinear pre-chirp NLC2 is added by element 150B-2 to partially amplified light $S_{B2}$ to generate amplified light $S_{B3}$) to compensate for the individual SPM effect generated by an associated fiber amplifier 130B-1, 130B-2 ... 130B-n. For example, nonlinear pre-chirp NLC1 compensates for the SPM characteristics of amplifier 130B-1, and is added by element 150B-1 to seed light $S_0$ to generate modified seed light $S_{B1}$. Similarly, nonlinear pre-chirp NLC2 compensates for the SPM characteristics of amplifier 130B-2, and is added by element 150B-2 to partially amplified light $S_{B2}$ to generate amplified light $S_{B3}$. The cumulative effect of nonlinear chirp elements 150B-1, 150B-2 ... is similar to that of the single chirp element embodiment, but the multiple-element approach simplifies the compensating nonlinear chirp calculation by addressing the SPM characteristics of each fiber amplifier individually (i.e., instead of having to calculate a compensating nonlinear chirp for the cumulative SPM of multiple series-connected amplifiers).

Figure 8:
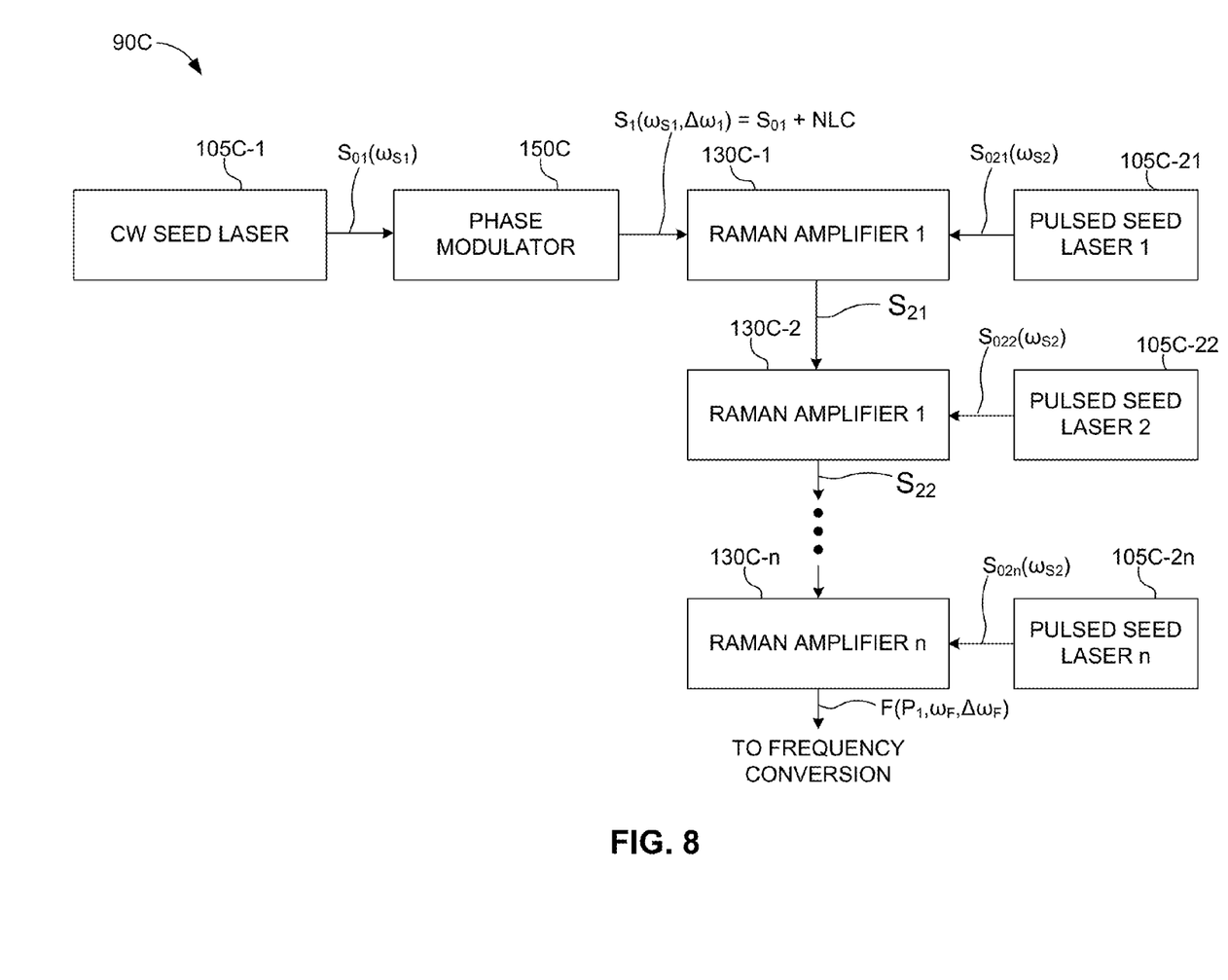
FIG. 8 is a simplified block diagram showing a laser system according to yet another embodiment of the present invention.
Figure 9A:
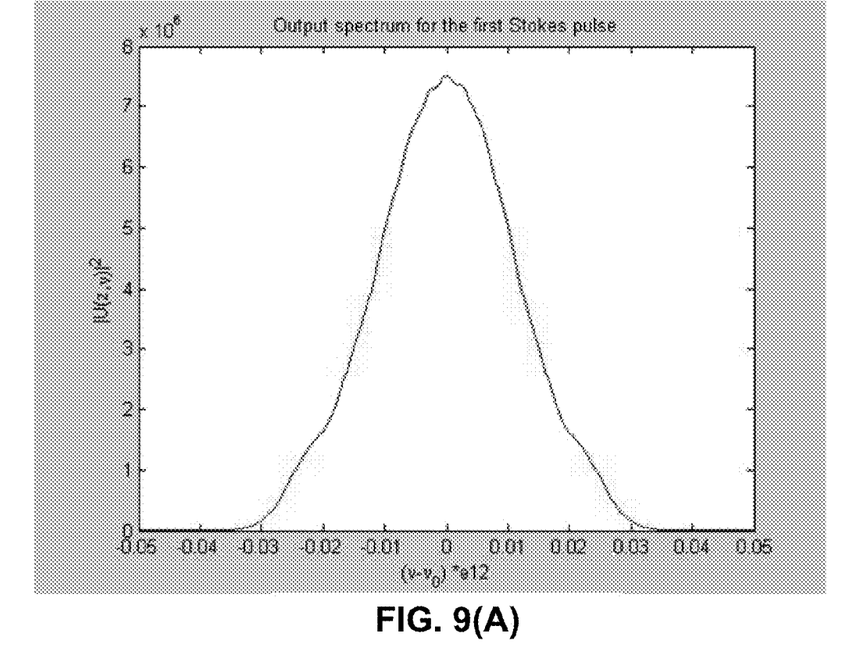
FIGS. 9(A) and 9(B) are output spectrum diagrams showing light generated by the laser system of FIG. 8.
Figure 9B:
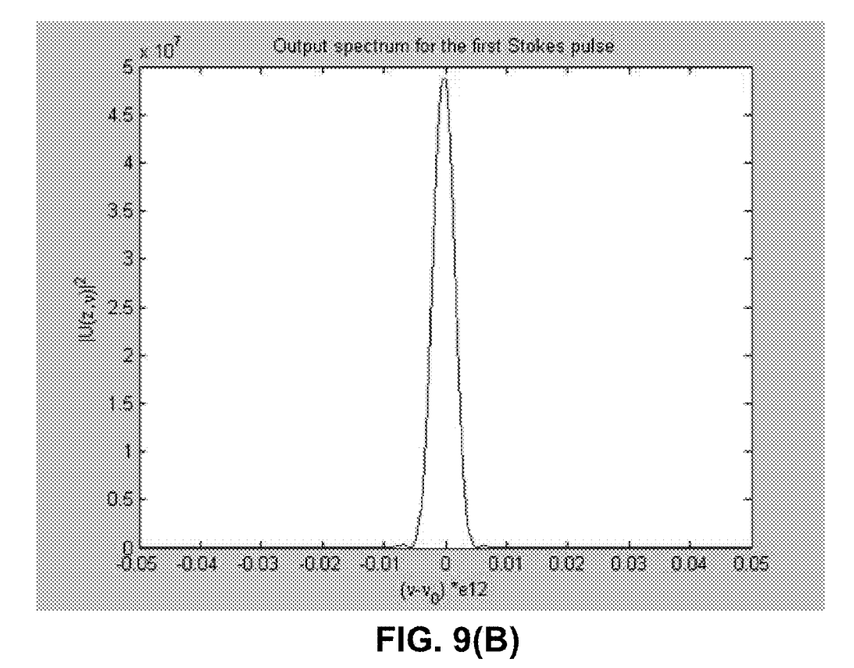

FIG. 8 shows a portion of a laser system 90C according to another embodiment of the present invention in which a fiber-based fundamental laser system 100B utilizes series-connected Raman amplifiers 130C-1, 130C-2 ... 130C-n. In this case, seed laser 105C-1 is implemented by a continuous wave (CW) laser (e.g., one of a solid state laser, a diode laser and a quantum dot laser), and the nonlinear chirp element is implemented by a phase modulator 150C disposed in the optical path between (first) Raman amplifier 130C-1 and CW seed laser 105C such that Raman amplifier 130C-1 receives both CW seed light $S_{O1}$ and a nonlinear chirp NLC from phase modulator 150C. Fundamental laser system 100B also includes multiple pulse-type pump seed lasers 105C-21, 105C-22 ... 105C-2n (e.g., gain-switched laser diodes or pulsed light oscillators) that respectively supply pulse-type pump seed light to respective Raman amplifiers 130C-1, 130C-2 ... 130C-n. For example, pulse-type pump seed laser 105C-21 supplies pulse-type pump seed light $S_{O21}$ to Raman amplifier 130C-1, and pulse-type pump seed laser 105C-22 supplies pulse-type pump seed light $S_{O22}$ to Raman amplifier 130C-2. FIGS. 9(A) and 9(B) show results of using a nonlinear chirp to compensate for Cross phase modulation (XPM) for a Raman amplifier in accordance with the embodiment shown in FIG. 8. XPM is 2× worse than SPM obtained in standard fiber lasers for the same peak powers. A benefit of utilizing this Raman amplifier approach is that high powers at wavelengths beyond those that are available with standard fiber lasers are more practical. One or more Raman shifts can be used to increase the wavelength.

Although the present invention has been described with respect to certain specific embodiments, it will be clear to those skilled in the art that the inventive features of the present invention are applicable to other embodiments as well, all of which are intended to fall within the scope of the present invention.

The invention claimed is:

1. A fiber-based fundamental light source for generating fundamental light at a nominal fundamental frequency a laser system, the fiber-based fundamental light source comprising:
   one or more seed lasers including means for generating seed light having an initial peak power and an initial spectral bandwidth, and for transmitting the seed light along an optical path;
   one or more amplifiers disposed in the optical path and including means for amplifying the seed light generated by said one or more seed lasers such that amplified light output from the one or more amplifiers has a fundamental peak power that is substantially higher than the initial peak power; and
   one or more nonlinear chirp elements disposed in the optical path and including means for modifying one of the seed light and the amplified light to include one or more nonlinear chirps that compensate for Self Phase Modulation (SPM) characteristics of the one or more amplifiers,
   wherein each of said one or more nonlinear chirp elements comprises one of a Bragg grating, a fiber Bragg grating and an electro-optic modulator, and
   wherein said one or more nonlinear chirp elements comprise means for generating said nonlinear pre-chirp with a nonlinearity on the order of $x^2$ or higher.

2. The fiber-based fundamental light source of claim 1, wherein said one or more nonlinear chirp elements comprise means for generating said nonlinear pre-chirp $U(0,T)$ having time-based frequency characterized by the equation $$U(0, T) = \exp\left[-\frac{(1 + i(C + DT + ET^2 + FT^3 + GT^4 + \ldots\ ))\, T^2}{2} \frac{}{T_0^2}\right]$$

where T is time, i indicates an imaginary part of the amplitude that contains a phase term, and wherein at least one of one of E, F and G is non-zero.

3. The fiber-based fundamental light source of claim 1, wherein said one or more seed lasers and said one or more amplifiers comprise means for generating said fundamental light such that said nominal fundamental frequency is approximately 1 μm.

4. The fiber-based fundamental light source of claim 1, wherein each of said one or more seed lasers comprises one of a pulsed light oscillator, a solid state laser, a diode laser, a gain-switched laser diode, and a quantum dot laser.

5. The fiber-based fundamental light source of claim 1, wherein said one or more amplifiers comprise one of a doped fiber amplifier and a Raman amplifier.

6. The fiber-based fundamental light source of claim 1, further comprising a pump seed laser for transmitting pump seed light to said one or more amplifiers.

7. The fiber-based fundamental light source of claim 1, wherein said one or more nonlinear chirp elements are disposed between the one or more seed lasers and the one or more amplifiers in the optical path such that modified seed light exiting the one or more nonlinear chirp elements has a modified power that is substantially equal to said initial peak power and a modified spectral bandwidth, that is different from said initial spectral bandwidth, and
wherein said one or more amplifiers includes means for amplifying the modified seed light such that said nominal fundamental frequency of said fundamental light is in the UV-DUV range.

8. The fiber-based fundamental light source of claim 7, wherein said one or more amplifiers comprises a plurality of amplifiers connected in series in said optical path.

9. The fiber-based fundamental light source of claim 1, wherein said one or more amplifiers comprises a plurality of amplifiers including a first amplifier and a second amplifier, and
wherein said one or more nonlinear chirp elements comprise at least one nonlinear chirp elements disposed between said first and second amplifiers in said optical path.

10. The fiber-based fundamental light source of claim 1, wherein said one or more seed lasers comprises a continuous wave (CW) laser for generating CW seed light and a pulsed laser for generating pulsed pump seed light,
wherein said one or more amplifiers comprises a Raman amplifier disposed to receive said CW seed light and said pulsed pump seed light,
wherein said one or more nonlinear chirp elements comprises a phase modulator disposed in the optical path between the Raman amplifier and the CW laser such that said Raman amplifier receives both said CW seed light and said nonlinear chirp from said phase modulator.

11. The fiber-based fundamental light source of claim 10, wherein said CW laser comprises one of a solid state laser, a diode laser and a quantum dot laser, and
wherein said pulsed laser comprises one of a gain-switched laser diode and a pulsed light oscillator.

12. The fiber-based fundamental light source of claim 10, wherein said said one or more amplifiers comprises a second Raman amplifier disposed in the optical path to receive amplified light output from said Raman amplifier, and
wherein said one or more seed lasers further comprises a second pulsed laser disposed to transmit second pulsed pump seed light into said second Raman amplifier.

13. A fiber-based fundamental light source for generating fundamental light at a nominal fundamental frequency a laser system, the fiber-based fundamental light source comprising:
one or more seed lasers including means for generating seed light having an initial peak power and an initial spectral bandwidth, and for transmitting the seed light along an optical path;
one or more amplifiers disposed in the optical path and including means for amplifying the seed light generated by said one or more seed lasers such that amplified light output from the one or more amplifiers has a fundamental peak power that is substantially higher than the initial peak power; and
one or more nonlinear chirp elements disposed in the optical path and including means for modifying one of the seed light and the amplified light to include one or more nonlinear chirps that compensate for Self Phase Modulation (SPM) characteristics of the one or more amplifiers,
wherein said one or morenonlinear chirp elements includes means for generating said nonlinear chirp such that the nonlinear chirp compensates for said SPM characteristics of the one or more amplifiers such that said fundamental light generated by said laser system has a fundamental spectral bandwidth that is in a range defined by five times said initial spectral bandwidth of said seed light.

14. A method for generating fundamental light using a fiber-based laser system, the method comprising:
generating seed light having an initial spectral bandwidth;
amplifying the seed light using one or more fiber-based amplifiers to produce amplified light having a peak power that is substantially higher than the initial peak power; and
modifying one of the seed light and the amplified light to include a nonlinear chirp,
wherein the nonlinear chirp has a nonlinearity on the order of $x^2$ or higher and substantially entirely compensates for Self Phase Modulation (SPM) characteristics of said one or more fiber-based amplifiers such that said fundamental light has a fundamental spectral bandwidth that is within a range defined by five times said initial spectral bandwidth.

15. The method of claim 14, wherein modifying one of the seed light and the amplified light to include a nonlinear chirp comprises generating said nonlinear pre-chirp U(0,T) having time-based frequency characterized by the equation $$U(0, T) = \exp\left[-\frac{(1 + i(C + DT + ET^2 + FT^3 + GT^4 + \ldots\ ))}{2}\frac{T^2}{T_0^2}\right]$$

where T is time, i indicates an imaginary part of the amplitude that contains a phase term, and wherein at least one of one of E, F and G is non-zero.

16. The method of claim 14,
wherein modifying comprises modifying said seed light, and
wherein amplifying comprises amplifying the modified seed light.

17. The method of claim 14,
wherein modifying comprises modifying said amplified light to include said nonlinear chirp, and
wherein the method further comprises amplifying said modified amplified light.

18. The method of claim 14,
- wherein generating seed light comprises generating continuous wave (CW) seed light and pulsed pump seed light,
- wherein modifying comprises modifying said CW seed light, and
- wherein amplifying the seed light comprises directing said modified CW seed light and said pulsed pump seed light into a Raman amplifier.

* * * * *